United States Patent
Ota et al.

[11] Patent Number: 6,156,801
[45] Date of Patent: Dec. 5, 2000

[54] 2-PHENOXYANILINE DERIVATIVES

[75] Inventors: Tomomi Ota; Misa Nakanishi; Minoru Taguchi; Kazuyuki Tomisawa, all of Tokyo, Japan

[73] Assignee: Taisho Pharmaceutical Co., Ltd., Japan

[21] Appl. No.: 09/381,039

[22] PCT Filed: Mar. 26, 1998

[86] PCT No.: PCT/JP98/01367

§ 371 Date: Sep. 15, 1999

§ 102(e) Date: Sep. 15, 1999

[87] PCT Pub. No.: WO98/43943

PCT Pub. Date: Oct. 8, 1998

[30] Foreign Application Priority Data

Mar. 27, 1997 [JP] Japan ................................. 9-074288

[51] Int. Cl.[7] ............. A61K 31/136; A61K 31/167; A61K 31/277; C07C 217/90; C07C 237/40; C07C 255/58

[52] U.S. Cl. .................. 514/646; 514/524; 514/535; 514/629; 558/424; 560/45; 564/221; 564/430

[58] Field of Search .................... 558/424; 560/45; 564/221, 430; 514/524, 535, 629, 646

[56] References Cited

U.S. PATENT DOCUMENTS 5,006,660  4/1991  Yamakawa ................ 546/316
5,556,860  9/1996  Muraoka et al. ............ 514/258

FOREIGN PATENT DOCUMENTS 02-076842  3/1990  Japan .
05-194400  3/1993  Japan .
07-041465  2/1995  Japan .

OTHER PUBLICATIONS

Coutts, I.G.C. et al. Synthesis of Spiroheterocycles by Oxidative Coupling of Phenolic Sulphonamides. J. Chem. Soc. Chem. Commun. 1980, pp. 949–950.

*Primary Examiner*—Michael G. Ambrose
*Attorney, Agent, or Firm*—Lorusso & Loud

[57] ABSTRACT

A 2-phenoxyaniline derivative represented by the formula:

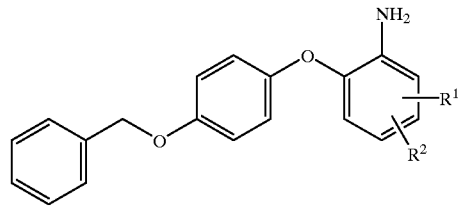

wherein $R^1$ is a hydrogen atom, an amino group or an $NHCOR^3$ group, $R^2$ is a halogen atom, an amino group, a cyano group, a $C_{1-6}$ alkyl group, a $C_{1-3}$ perfluoroalkyl group, an $NHCOR^3$ group, a $CH_2OR^4$ group, an $OCH_2R^5$ group or a $COR^6$ group, $R^3$ is a $C_{1-6}$ alkyl group, $R^4$ is a hydrogen atom or a $C_{1-6}$ alkyl group, $R^5$ is a hydrogen atom, a $C_{1-6}$ alkyl group, a $C_{1-5}$ aminoalkyl group, a $C_{2-7}$ alkoxycarbonyl group or a carbamoyl group, and $R^6$ is a $C_{1-6}$ alkyl group or a $C_{3-8}$ cycloalkyl group which is unsubstituted or substituted by a halogen atom, an amino group, a cyano group or a straight or branched $C_{1-6}$ alkyl group; or a pharmaceutically acceptable salt thereof.

9 Claims, No Drawings

2-PHENOXYANILINE DERIVATIVES

TECHNICAL FIELD

The present invention relates to phenoxyaniline derivatives or pharmaceutically acceptable salts thereof having an inhibitory action on a $Na^+/Ca^{2+}$ exchange system.

BACKGROUND ART

Among prior art compounds which inhibit a $Na^+/Ca^{2+}$ exchange system selectively and prevent overload of $Ca^{2+}$ in cells regarded as important in the cell injury mechanism after ischemia or reperfusion, there are known compounds having a quinazoline skeleton as described in Japanese Patent Kokai 7-41465. However, there is no report that the compounds having a phenoxyaniline skeleton as shown in the present invention have an inhibitory action on a $Na^+/Ca^{2+}$ exchange system.

DISCLOSURE OF THE INVENTION

As a result of extensive researches on the compounds having an inhibitory action on a $Na^+/Ca^{2+}$ exchange system, the present inventors have found that some kind of compounds having a phenoxyaniline skeleton meet said object, and the present invention has been accomplished based on the findings.

That is, the present invention is directed to a 2-phenoxylaniline derivative represented by Formula (1):

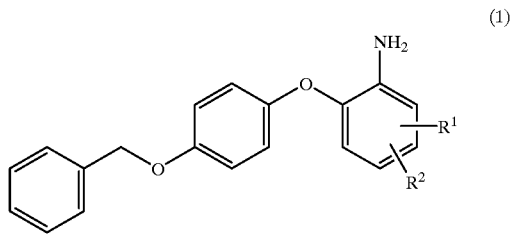

(1)

wherein $R^1$ is a hydrogen atom, an amino group or an $NHCOR^3$ group, $R^2$ is a halogen atom, an amono group, a cyano group, a $C_{1-6}$ alkyl group, a $C_{1-3}$ perfluoroalkyl group, an $NHCOR^3$ group, a $CH_2OR^4$ group, an $OCH_2R^5$ group or a $COR^6$ group, $R^3$ is a $C_{1-6}$ alkyl group, $R^4$ is a hydrogen atom or a $C_{1-6}$ alkyl group, $R^5$ is a hydrogen atom, a $C_{1-6}$ alkyl group, a $C_{1-5}$ aminoalkyl group, a $C_{2-7}$ alkoxycarbonyl group or a carbamoyl group, and $R^6$ is a $C_{1-6}$ alkyl group or a $C_{3-8}$ cycloalkyl group which is unsubstituted or substituted by a halogen atom, an amino group, a cyano group or a $C_{1-6}$ alkyl group; or a pharmaceutically acceptable salt thereof.

Furthermore, the present invention is directed to a pharmaceutical composition containing the above-mentioned compound or the pharmaceutically acceptable salt thereof as an effective component.

Furthermore, the present invention is directed to a pharmaceutical composition for the treatment or prevention of ischemic heart diseases, ischemic cerebral diseases or ischemic renal diseases containing the above-mentioned compound or the pharmaceutically acceptable salt thereof as an effective component.

Furthermore, the present invention is directed to use of the above-mentioned compound or the pharmaceutically acceptable salt thereof for the manufacture of a pharmaceutical composition for the treatment or prevention of ischemic heart diseases, ischemic cerebral diseases or ischemic renal diseases.

Furthermore, the present invention is directed to a method for the treatment or prevention of ischemia heart diseases, ischemic cerebral diseases or ischemic renal diseases which includes the step of administering a pharmacologically effective amount of the above-mentioned compound or the pharmaceutically acceptable salt thereof to a human.

Furthermore, the present invention is directed to a pharmaceutical composition for the protection of cells during thrombolytic therapy, angioplasty, bypass operation of coronary artery or organ transplantation containing the above-mentioned compound or the pharmaceutically acceptable salt thereof as an effective component.

Furthermore, the present invention is directed to use of the above-mentioned compound or the pharmaceutically acceptable salt thereof for the manufacture of a pharmaceutical composition for the protection of cells during thrombolytic therapy, angioplasty, bypass operation of coronary artery or organ transplantation.

Furthermore, the present invention is directed to a method for the protection of cells during thrombolytic therapy, angioplasty, bypass operation of coronary artery or organ transplantation which includes the step of administering a pharmacologically effective amount of the above-mentioned compound or the pharmaceutically acceptable salt thereof to a human.

In the present invention, the halogen atom refers to a fluorine atom, a chlorine atom, a bromine atom or an iodine atom.

The $C_{1-6}$ alkyl group refers to a straight or branched $C_{1-6}$ alkyl group, and specific examples thereof are a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group and an isohexyl group.

Specific examples of the $C_{1-3}$ perfluoroalkyl group are a trifluoromethyl group and a pentafluoroethyl group.

The $C_{1-5}$ aminoalkyl group refers to a straight or branched $C_{1-5}$ aminoalkyl group, and specific examples thereof are an aminomethyl group, a 2-aminoethyl group, a 3-aminopropyl group, a 4-aminobutyl group and a 5-aminopentyl group.

The $C_{2-7}$ alkoxycarbonyl group refers to a straight or branched $C_{2-7}$ alkoxycarbonyl group, and specific examples thereof are a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group and a hexyloxycarbonyl group.

Specific examples of the $C_{3-8}$ cycloalkyl group are a cyclopropyl group, a cyclobutyl group, a cyclo-pentyl group and a cyclohexyl group.

Preferred phenoxyaniline derivatives of the present invention are compounds of Formula (1) wherein $R^1$ is a hydrogen atom.

In the present invention, $R^2$ is preferably an $OCH_2R^5$ group (wherein $R^5$ is a hydrogen atom or a $C_{1-6}$ alkyl group), and more preferably an $OCH_2R^5$ group (wherein $R^5$ is a hydrogen atom or a $C_{1-2}$ alkyl group).

The phenoxyaniline derivatives of the present invention can be prepared, for example, according to the following preparation scheme (wherein $R^1$ and $R^2$ are as defined above, $R^7$ is a nitro group when $R^1$ is an amino group, or the same substituent as $R^1$ when $R^1$ is a substituent other than an amino group, $R^8$ is a nitro group when $R^2$ is an amino group, or the same substituent as $R^2$ when $R^2$ is a substituent other than an amino group, and X is a fluorine atom or a chlorine atom).

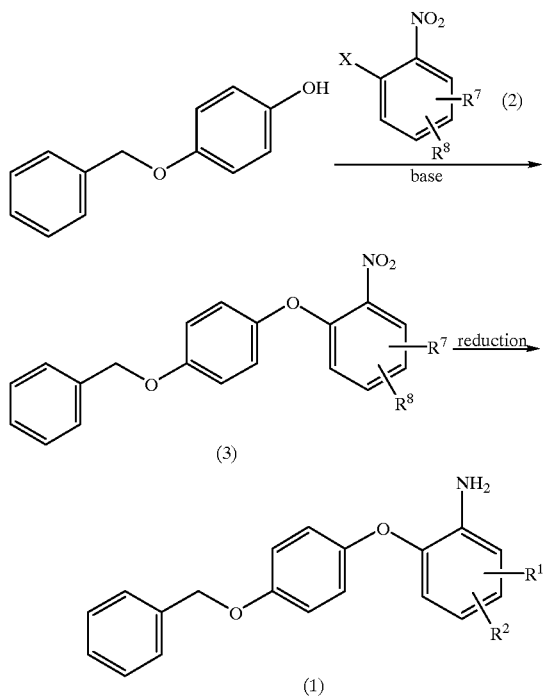

That is, 4-(benzyloxy)phenol and a compound represented by Formula (2) are reacted in the presence of a base to give a compound represented by Formula (3). Examples of the base to be used herein are organic and inorganic bases such as potassium tert-butoxide, sodium hydroxide or sodium hydride. As the reaction solvent can be used N,N-dimethylformamide or tetrahydrofuran, and the reaction temperature is from room temperature to the reflux temperature.

Then, the compound represented by Formula (3) is reduced to give a compound of the present invention represented by Formula (1). As the reducing agent can be used herein iron-ammonium chloride, iron-acetic acid, palladium carbon-hydrogen, lithium aluminum hydride, nickel chloride-sodium borohydride, etc. As the reaction solvent can be used herein water, methanol, ethanol, tetrahydrofuran, etc., and they can be used alone or in admixture. The reaction temperature is preferably from 0° C. to the reflux temperature.

The phenoxyaniline derivative or the pharmaceutically acceptable salt thereof of the present invention is generally administered orally or parenterally to a human.

In case of oral administration, the phenoxyaniline derivative or the pharmaceutically acceptable salt thereof is mixed with a filler, a disintegrator, a binder, a lubricant, a coating agent, etc., to form granules, powders, capsules or tablets, which then can be administered; and in case of parenteral administration, it can be administered in the form of injectable preparations, drip infusion preparations or suppositories.

The above-mentioned pharmaceutical preparations can be produced by an ordinary preparation method such as agitation granulation, fluidized bed granulation or disintegration granulation.

Examples of the filler are mannitol, xylitol, sorbitol, glucose, sucrose, lactose and crystalline cellulose.

Examples of the disintegrator are low substituted hydroxypropyl cellulose, carboxymethyl cellulose, carboxymethyl cellulose calcium and carboxymethyl cellulose sodium.

Examples of the binder are methyl cellulose, hydroxypropyl cellulose, hydroxypropylmethyl cellulose, polyvinylpyrrolidone, gelatin, arabic gum and ethyl cellulose.

Examples of the lubricant are stearic acid, magnesium stearate and calcium stearate.

If necessary, an anti-oxidant, a coating agent, a coloring agent, a corrigent, a surface active agent, a plasticizer and others can be added to the pharmaceutical preparations.

The dose of the effective component of the pharmaceutical preparation in the present invention can be varied depending on the age, body weight or administration route, but it is usually from 0.1 to 1000 mg/day to an adult, which can be administered in a single dose or divided doses.

INDUSTRIAL APPLICABILITY

The compounds of the present invention have an inhibitory action on a $Na^+/Ca^{2+}$ exchange system, thus, they prevent overload of $Ca^{2+}$ in cells, are useful for the treatment or prevention of ischemic heart diseases such as myocardial infarction, ischemic cerebral diseases such as cerebral infarction, or ischemia renal diseases, and further useful for the protection of cells during thrombolytic therapy, angioplasty, bypass operation of coronary artery or organ transplantation.

BEST MODE OF CARRYING OUT THE INVENTION

The present invention is illustrated in more detail by the following examples and experiments. Furthermore, the structural formula which represents the compounds prepared in Examples 1 to 24 is shown in Table 1.

TABLE 1

Structural Formula

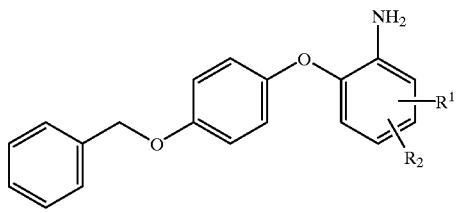

| Example No. | $R^1$ | $R^2$ | |
|---|---|---|---|
| 1 | H | 5-$OCH_3$ | hydrochloride |
| 2 | H | 5-$CH_3$ | — |
| 3 | H | 5-$CF_3$ | — |
| 4 | H | 3-Cl | hydrochloride |
| 5 | H | 4-$CH_3$ | — |
| 6 | H | 5-Cl | — |
| 7 | H | 3-$CH_3$ | hydrochloride |
| 8 | 3-$NH_2$ | 5-$CF_3$ | dihydrochloride |
| 9 | H | 5-CO-c-$C_3H_5$ | — |
| 10 | 4-$NHCOCH_3$ | 5-Cl | hydrochloride |
| 11 | H | 5-$COCH_3$ | — |
| 12 | 5-$NH_2$ | 4-$CH_3$ | — |
| 13 | H | 5-F | hydrochloride |
| 14 | H | 3-$NH_2$ | dihydrochloride |
| 15 | H | 5-CN | hydrochloride |
| 16 | 3-$NH_2$ | 5-CN | dihydrochloride |
| 17 | H | 5-$OCH_2CH_3$ | hydrochloride |
| 18 | H | 5-$OCH_2CH_2CH_3$ | — |
| 19 | H | 5-$OCH_2CONH_2$ | hydrochloride |
| 20 | H | 5-$OCH_2CO_2CH_3$ | hydrochloride |
| 21 | H | 5-$CH_2OH$ | — |

TABLE 1-continued

Structural Formula

| Example No. | R¹ | R² | |
|---|---|---|---|
| 22 | H | 5-CH$_2$OCH$_3$ | — |
| 23 | H | 5-NHCOCH$_2$CH$_2$CH$_3$ | — |
| 24 | H | 5-OCH$_2$CH$_2$CH$_2$NH$_2$ | hydrochloride |

EXAMPLE 1

2-[4-(Benzyloxy)phenoxy]-5-methoxyaniline hydrochloride (1) To a solution of 4-(benzyloxy)phenol (2.00 g, 10 mmol) in N,n-dimethylformamide (20 ml) was added potassium tert-butoxide (1.12 g, 10 mmol), followed by stirring for 10 minutes. To the reaction solution was added 4-chloro-3-nitroanisole (1.88 g, 10 mmol), followed by stirring at 150° C. for 6 hours. After allowing to stand overnight, the reaction solution was poured into water and extracted with ethyl acetate. After drying subsequent to washing with water and a saturated aqueous sodium chloride solution, the solvent was evaporated under reduced pressure. The resulting crude crystals were recrystallized from ethanol to give 4-[4-(benzyloxy)phenoxy]-3-nitroanisole (2.13 g).

m.p. 88–89.5° C.

(2) To a solution of 4-[4-(benzyloxy)phenoxy]-3-nitroanisole (1.23 g, 3.5 mmol) in ethanol (20 ml) were added an iron powder (0.90 g, 16.1 mg-atom) and a solution of ammonium chloride (0.11 g, 2.1 mmol) in water (2 ml), followed by reflux for 3 hours. The insoluble matter was filtered, and the filtrate was poured into water, followed by extraction with ethyl acetate. The organic layer was washed with water, then with a saturated aqueous sodium chloride solution and dried, and thereafter the solvent was evaporated under reduced pressure. The residue was dissolved in a small amount of ethyl acetate, and the resulting solution was, after addition of 4N-hydrogen chloride/acetic acid solution (2 ml), stirred for 30 minutes. The precipitating crystals were collected by filtration and dried under reduced pressure to give the title compound (0.65 g).

m.p. 170–170.5° C.

The following compounds of Examples 2 to 16 were synthesized in the same manner as in Example 1, and these instrumental measurement values were shown below.

EXAMPLE 2

2-[4-(Benzyloxy)phenoxy]-5-methylaniline
m.p. 105.5–106.5° C.

EXAMPLE 3

2-[4-(Benzyloxy)phenoxy]-5-(trifluoromethyl)aniline
m.p. 100–101.5° C.

EXAMPLE 4

2-[4-(Benzyloxy)phenoxy]-3-chloroaniline hydrochloride
m.p. 176–177° C.

EXAMPLE 5

2-[4-(Benzyloxy)phenoxy]-4-methylaniline
m.p. 116.5–117.5° C.

EXAMPLE 6

2-[4-(Benzyloxy)phenoxy]-5-chloroaniline
m.p. 107–108° C.

EXAMPLE 7

2-[4-(Benzyloxy)phenoxy]-3-methylaniline hydrochloride
m.p. 193.5–194° C.

EXAMPLE 8

2-[4-(Benzyloxy)phenoxy-5-(trifluoromethyl)-1 3-phenylenediamine dihydrochloride
m.p. 186.5–187° C.

EXAMPLE 9

2-[4-(Benzyloxy)phenoxy]-5-(cyclopropylcarbonyl)-aniline
m.p. 138–140° C.

EXAMPLE 10

4-Acetamido-2-[4-(benzyloxy)phenoxy]-5-chloroaniline hydrochloride $^1$H-NMR (DMSO-d$_6$, 200 MHz) δ (ppm); 1.99 (s, 3H), 5.08 (s, 2H), 7.05 (s, 4H), 7.11 (s, 1H), 7.30–7.50 (m, 6H), 8.18 (bs, 3H), 9.41 (s, 1H).

EXAMPLE 11

5-Acetyl-2-[4-(benzyloxy)phenoxy]aniline
m.p. 135.5–136.5° C.

EXAMPLE 12

4-[4-(Benzyloxy)phenoxy]-6-methyl-1,3-phenylenediamine $^1$H-NMR (CDCl$_3$, 200 MHz) δ (ppm); 2.03 (s, 3H), 3.50 (bs, 4H), 5.00 (s, 2H), 6.18 (s, 1H), 6.60 (s, 1H), 6.86 (s, 4H), 7.25–7.48 (m, 5H).

EXAMPLE 13

2-[4-(Benzyloxy)phenoxy]-5-fluoroaniline hydrochloride
m.p. 176.5–177° C.

EXAMPLE 14

2-[4-(Benzyloxy)phenoxy]-1,3-phenylenediamine dihydrochloride
m.p. 173–173.5° C.

EXAMPLE 15

2-[4-(Benzyloxy)phenoxy]-5-cyanoaniline hydrochloride
m.p. 170–171° C.

EXAMPLE 16

2-[4-(Benzyloxy)phenoxy]-5-cyano-1,3-phenylenediamine dihydrochloride
m.p. 160–161.50° C.

EXAMPLE 17

2-[4-(Benzyloxy)phenoxy-5-ethoxyaniline hydrochloride (1) To a solution of 4-chloro-3-nitrophenol (5.00 g, 29 mmol) in acetone (50 ml) were added ethyl iodide (4.95 g, 32 mmol) and potassium carbonate (4.37 g, 32 mmol), followed by stirring at room temperature for 20 hours. After filtration of the insoluble matter, the filtrate was subjected to evaporation under reduced pressure to remove the solvent, and the residue was purified by silica gel column chromatography (eluent; chloroform) to give 4-ethoxy-1-chloro-2-nitrobenzene (5.71 g).

(2) The title compound was obtained from 4-(benzyloxy) phenol and 4-ethoxy-1-chloro-2-nitrobenzene in the same manner as in Example 1.

m.p. 164–164.5° C.

The following compounds of Examples 18 to 20 were synthesized in the same manner as in Example 1, and these instrumental measurement values were shown below.

EXAMPLE 18

2-[4-(Benzyloxy)phenoxy-5-propoxyaniline m.p. 103–103.5° C.

EXAMPLE 19

3-Amino-4-[4-(benzyloxy)phenoxy]phenoxy-acetamide hydrochloride m.p. 198.5–199.5° C.

EXAMPLE 20

Methyl 3-amino-4-[4-(benzyloxy)-phenoxy] phenoxyacetate hydrochloride m.p. 179–180° C.

EXAMPLE 21

3-Amino-4-[4-(benzyloxy)phenoxy]benzyl alcohol (1) 4-[4-(Benzyloxy)phenoxy]-3-nitro-benzaldehyde was obtained from 4-(benzyloxy)phenol and 4-chloro-3-nitrobenzaldehyde in the same manner as in Example 1(1).

m.p. 111–112.5° C.

(2) To a solution of 4-[4-(benzyloxy)-phenoxy]-3-nitrobenzaldehyde (2.48 g, 7.1 mmol) in ethanol (100 ml) was added sodium borohydride (0.27 g, 7.3 mmol), followed by stirring at room temperature for 2 hours. The reaction solution was poured into water and extracted with ethyl acetate. The solvent was dried and evaporated under reduced pressure. The residue was purified by silica gel column chromatography [eluent; chloroform - ethyl acetate (4:1)] to give 4-[4-(benzyloxy)phenoxy]-3-nitrobenzyl alcohol (2.48 g).

m.p. 72–73° C.

(3) The title compound was obtained from 4-[4-(benzyloxy)phenoxy]-3-nitrobenzyl alcohol in the same manner as in Example 1(2).

m.p. 128–130° C.

EXAMPLE 22

2-[4-(Benzyloxy)phenoxy]-5-(methoxymethyl)aniline (1) To a solution of 4-[4-(benzyloxy)-phenoxy]-3-nitrobenzyl alcohol (9.43 g, 26.9 mmol) in chloroform (60 ml) was added thionyl chloride (2 ml), followed by stirring at room temperature for 6 hours. After allowing to stand overnight, the reaction solution was washed with water and dried, and the solvent was evaporated under reduced pressure. The residue was purified by silica gel column chromatography [eluent; hexane - chloroform (1:1)] to give 4-[4-(benzyloxy)-phenoxy]-3-nitrobenzyl chloride (7.63 g).

m.p. 106–107° C.

(2) 60% Oily sodium hydride (0.22 g, 5.5 mmol) was added to methanol (50 ml) under ice-cooling, and after stirring at room temperature for 30 minutes, 4-[4-(benzyloxy)phenoxy]-3-nitrobenzyl chloride (1.00 g, 2.7 mmol) was added thereto, followed by stirring for 3 hours. The reaction solution was poured into water and extracted with ethyl acetate. After drying, the solvent was evaporated under reduced pressure, and the residue was purified by silica gel column chromatography [eluent; hexane - chloroform (1:1)] to give 1-[4-benzyloxy)phenoxy]-4-(methoxymethyl)-2-nitrobenzene (0.92 g).

(3) The title compound was obtained from 1- [4-(benzyloxy)phenoxy]-4-(methoxymethyl)-2-nitrobenzene in the same manner as in Example 1(2).

m.p. 79.5–81° C.

EXAMPLE 23

N-[3-Amino-4-[4-(benzyloxy)phenoxy]phenyl]-butyramide (1) To a solution of 4-chloro-3-nitroaniline (3.45 g, 30 mmol) in chloroform (100 ml) was added butyric anhydride (5 ml), followed by stirring at room temperature for 2 hours. After allowing to stand overnight, a saturated aqueous sodium carbonate solution was added, followed by stirring for 30 minutes. The organic layer was separated and dried, the solvent was evaporated under reduced pressure, and the residue was purified by silica gel column chromatography [eluent; hexane - chloroform (1:1)] to give N-(4-chloro-3-nitrophenyl)butyramide (4.66 g).

(2) The title compound was obtained from 4-(benzyloxy) phenol and N-(4-chloro-3-nitrophenyl)-butyramide in the same manner as in Example 1.

m.p. 122.5–123.50° C.

EXAMPLE 24

3- [3-Amino-4-[4-(benzyloxy)phenoxy]phenoxy]-propylamine hydrochloride (1) To a solution of 4-chloro-3-nitrophenol (5.00 g, 29 mmol) in N,N-dimethylformamide (100 ml) were added N-(3-bromopropyl)phthalimide (9.27 g, 35 mmol) and potassium carbonate (4.93 g, 36 mmol), followed by stirring at 60° C. for 6 hours. After allowing to stand overnight, the reaction solution was poured into water, and the insoluble matter was collected by filtration and washed with ethyl acetate and dried under reduced pressure to give N-[3-(4-chloro-3-nitrophenoxy)-propyl]phthalimide (7.78 g).

(2) N-[3-[4-[4-(Benzyloxy)phenoxy]-3-nitrophenoxy] propyl]phthalimide was obtained from 4-(benzyloxy) phenol and N-[3-(4-chloro-3-nitrophenoxy)-propyl] phthalimide in the same manner as in Example 1(1).

m.p. 140–141° C.

(3) To a solution of N-[3-[4-[4-(benzyloxy)-phenoxy]-3-nitrophenoxy]propyl]phthalimide (2.06 g, 3.9 mmol) in methanol (60 ml) was added hydrazine monohydrate (2 ml), followed by stirring for 3 hours. After allowing to stand overnight, the reaction solution was poured into water and extracted with chloroform. After drying, the solvent was evaporated under reduced pressure, and the resulting residue was dissolved in a small amount of ethyl acetate. To this solution was added 4N hydrogen chloride/ethyl acetate solution (2 ml), followed by stirring at room temperature for 30 minutes. The precipitated crystals were collected by filtration and dried to give 3-[4-[4-(benzyloxy)-phenoxy]-3-nitrophenoxy]propylamine hydrochloride (1.42 g).

m.p. 179–181° C.

(4) The title compound was obtained from 3-[4-(benzyloxy)phenoxy]-3-nitrophenoxy]propylamine hydrochloride in the same manner as in Example 1(2).

$^1$H-NMR (DMSO-$d_6$, 200 MHz) δ (ppm); 2.02 (quint, J=6 Hz, 2H), 2.94 (sext, J=6 Hz, 2H), 4.00 (t, J=6 Hz, 2H), 5.06 (s, 2H), 6.60 (dd, J=2, 9 Hz, 1H), 6.76 (d, J=9 Hz, 1H), 6.88 (d, J=2 Hz, 1H), 6.92–7.08 (m, 4H), 7.28–7.50 (m, 5H), 8.09 (bs, 3H).

EXPERIMENT

Inhibitors Action on a $Na^+$/$Ca^{2+}$ Exchange System using Myosarcolemmal Vesicles Sarcolemmal vesicles which were prepared from the removed dog ventricular muscles by referring to the method described in the literature (L. R. Jones, Methods, Enzymol., 1988, 157, pp. 85) were used.

A $Na^+$/$Ca^{2+}$ exchange activity using the sarcolemmal vesicles was measured by referring to the method described in the literature (K. D. Philipson, et al., J. Biol. Chem., 1980, 255, pp. 6880). First, the sarcolemmal vesicles were suspended in a sodium-containing solution [160 mM sodium chloride, 20 mM hydrochloric acid (pH 7.4)] to make up to a protein concentration of 1.5 mg/ml, and allowed to stand for an hour to load $Na^+$ in the sarcolemmal vesicles. To 2.5 μl of the sarcolemmal vesicles was added 125 μl of a [$^{45}$Ca]-calcium chloride solution [20 μM [$^{45}$Ca]-calcium chloride, 160 mM potassium chloride and 20 mM Mops-Tris (pH 7.4)], and after 10 seconds, 900 μl of an ice-cooled lanthanum chloride solution [10 mM lanthanum chloride, 160 mM potassium chloride and 20 mM Mops-Tris (pH 7.4)] was added. The sarcolemmal vesicles were recovered on a nitrocellulose filter by suction filtration and washed three times with 900 μl of a lanthanum chloride solution. The concentration of $Ca^{2+}$ uptake in the sarcolemmal vesicles was determined by measuring a $^{45}Ca$ radioactivity by a scintillator. In addition, a $Na^+$/$Ca^{2+}$ exchange activity-independent $Ca^{2+}$ uptake in the sarcolemmal vesicles was determined by carrying out the same procedure using a potassium-containing solution [160 mM potassium chloride, 20 mM Tris-hydrochloric acid (pH 7.4)] instead of the sodium-containing solution.

The test compound was used as a dimethyl sulfoxide solution thereof, and its inhibitory effect was evaluated in comparison with the vehicle-treated group. The $IC_{50}$ value was determined from a dose inhibition curve of the test compound by using the minimum square method. The results are shown in Table 2.

TABLE 2

| Test Compounds | $IC_{50}$ (μM) |
|---|---|
| 1 | 1.1 |
| 14 | 8.2 |
| 17 | 2.5 |
| 19 | 14.0 |
| 20 | 2.8 |

What is claimed is:

1. A 2-phenoxyaniline derivative represented by Formula (1):

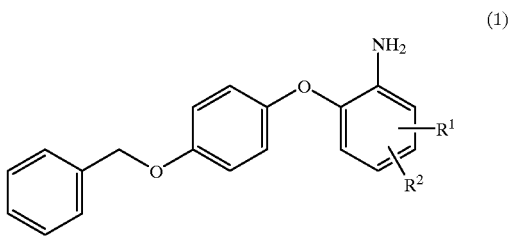

wherein $R^1$ is a hydrogen atom, an amino group or an $NHCOR^3$ group, $R^2$ is a halogen atom, an amino group, a cyano group, a $C_{1-6}$ alkyl group, a $C_{1-3}$ perfluoroalkyl group, an $NHCOR^3$ group, a $CH_2OR^4$ group, an $OCH_2R^5$ group or a $COR^6$ group, $R^3$ is a $C_{1-6}$ alkyl group, $R^4$ is a hydrogen atom or a $C_{1-6}$ alkyl group, $R^5$ is a hydrogen atom, a $C_{1-6}$ alkyl group, a $C_{1-5}$ aminoalkyl group, a $C_{2-7}$ alkoxycarbonyl group or a carbamoyl group, and $R^6$ is a $C_{1-6}$ alkyl group or a $C_{3-8}$ cycloalkyl group which is unsubstituted or substituted by a halogen atom, an amino group, a cyano group or a $C_{1-6}$ alkyl group; or a pharmaceutically acceptable salt thereof.

2. The 2-phenoxyaniline derivative or the pharmaceutically acceptable salt thereof according to claim 1, wherein $R^1$ in Formula (1) is a hydrogen atom.

3. The 2-phenoxyaniline derivative or the pharmaceuticallyacceptable salt thereof according to claim 1, wherein in Formula (1) $R^1$ is a hydrogen atom and $R^2$ is an $OCH_2R^5$ group in which $R^5$ is a hydrogen atom or a $C_{1-6}$ alkyl group.

4. A pharmaceutical composition containing the 2-phenoxyaniline derivative or the pharmaceutically acceptable salt thereof according to claim 1 as an effective component.

5. An inhibitor of a $Na^+$/$Ca^{2+}$ exchange system containing the 2-phenoxyaniline derivative or the pharmaceutically acceptable salt thereof according to claim 1 as an effective component.

6. A pharmaceutical composition for the treatment of ischemic heart diseases, ischemic cerebral diseases or ischemic renal diseases containing the 2-phenoxyaniline derivative or the pharmaceutically acceptable salt thereof according to claim 1 as an effective component.

7. A method for the treatment of ischemic heart diseases, ischemic cerebral diseases or ischemic renal diseases which includes the step of administering a pharmacologically effective amount of the 2-phenoxyaniline derivative or the pharmaceutically acceptable salt thereof according claim 1 to a human.

8. A pharmaceutical composition for the protection of cells during thrombolytic therapy, angioplasty, bypass operation of coronary artery or organ transplantation containing the 2-phenoxyaniline derivative or the pharmaceutically acceptable salt thereof according to claim 1 as an effective component.

9. A method for the protection of cells during thrombolytic therapy, angioplasty, bypass operation of coronary artery or organ transplantation which includes the step of administering a pharmacologically effective amount of the 2-phenoxyaniline derivative or the pharmaceutically acceptable salt thereof according to claim 1 to a human.

* * * * *

UNITED STATES PATENT AND TRADEMARK OFFICE
CERTIFICATE OF CORRECTION

PATENT NO. : 6,156,801 Page 1 of 1
APPLICATION NO. : 09/381039
DATED : December 5, 2000
INVENTOR(S) : Ota et al.

It is certified that error appears in the above-identified patent and that said Letters Patent is hereby corrected as shown below:

Col. 1, line 41, "amono" should read --amino--.

Col. 9, line 40, "hydrochloric" should read --Tris-hydrochloric--.

Col. 10, line 40, "callyacceptable" should read --cally acceptable--.

Signed and Sealed this

Twenty-second Day of August, 2006

JON W. DUDAS
*Director of the United States Patent and Trademark Office*